United States Patent
Shen

(10) Patent No.: US 11,461,554 B2
(45) Date of Patent: Oct. 4, 2022

(54) SEMANTIC CLASSIFICATION OF NUMERICAL DATA IN NATURAL LANGUAGE CONTEXT BASED ON MACHINE LEARNING

(71) Applicant: Siuvo Inc., Princeton, NJ (US)

(72) Inventor: Bin Shen, Princeton, NJ (US)

(73) Assignee: Siuvo Inc., Princeton, NJ (US)

( * ) Notice: Subject to any disclaimer, the term of this patent is extended or adjusted under 35 U.S.C. 154(b) by 318 days.

(21) Appl. No.: 16/633,863

(22) PCT Filed: Jul. 26, 2018

(86) PCT No.: PCT/US2018/043804
§ 371 (c)(1),
(2) Date: Jan. 24, 2020

(87) PCT Pub. No.: WO2019/023412
PCT Pub. Date: Jan. 31, 2019

(65) Prior Publication Data
US 2020/0218857 A1    Jul. 9, 2020

Related U.S. Application Data

(60) Provisional application No. 62/537,369, filed on Jul. 26, 2017.

(51) Int. Cl.
*G06F 40/30* (2020.01)
*G06F 40/289* (2020.01)
*G16H 10/60* (2018.01)
*G16H 50/20* (2018.01)
*G16H 20/00* (2018.01)
*G06N 3/04* (2006.01)
*G06N 3/08* (2006.01)

(52) U.S. Cl.
CPC ........... *G06F 40/30* (2020.01); *G06F 40/289* (2020.01); *G06N 3/0454* (2013.01); *G06N 3/0481* (2013.01); *G06N 3/08* (2013.01); *G16H 10/60* (2018.01); *G16H 20/00* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 9,824,692 B1 * | 11/2017 | Khoury | G10L 17/04 |
| 10,713,589 B1 * | 7/2020 | Zarandioon | G06N 20/00 |
| 2015/0006199 A1 | 1/2015 | Snider et al. | |
| 2016/0232142 A1 * | 8/2016 | Melnikov | G06F 40/151 |
| 2017/0206416 A1 | 7/2017 | Chen et al. | |
| 2020/0027560 A1 * | 1/2020 | Ling | G16H 10/60 |
| 2020/0097820 A1 * | 3/2020 | Song | G06F 40/30 |

* cited by examiner

*Primary Examiner* — Quynh H Nguyen
(74) *Attorney, Agent, or Firm* — Fox Rothschild LLP

(57) ABSTRACT

This application discloses methods and systems for semantic classification of numerical data in a natural language context. The methods and systems employ a machine learning model with a convolutional neural network as a feature detector and a feedforward neural network as a numerical data classifier.

13 Claims, 4 Drawing Sheets

At 5:33PM, she was afebrile with a temp of 96.5. However, her temperature 98.7 heart rate 82 blood pressure 160/62 Temp 98.6 P 94 BP 128/61 R 24 SaO2 96% 2L ED Course presented with Temp 98.4 HR 96 BP 118/54 RR |44|temperature| |was|104.2|degrees|Fahrenheit|heart| rate was 122.

◄──── *Six-word Window* ────►

FIG. 3

SEMANTIC CLASSIFICATION OF NUMERICAL DATA IN NATURAL LANGUAGE CONTEXT BASED ON MACHINE LEARNING

CROSS REFERENCE TO RELATED APPLICATION

This application is the U.S. national phase application of International Application No. PCT/US2018/043804, filed on Jul. 26, 2018, which claims priority under 35 U.S.C. § 119(e) to U.S. Provisional Patent Application Ser. No. 62/537,369, filed on Jun. 26, 2017, the disclosures of which are incorporated herein by reference in their entirety.

FIELD OF THE INVENTION

The present invention generally relates to the field of semantic classification of numerical data in its natural language context.

BACKGROUND OF THE INVENTION

Many documents contain important numerical data that present a significant value for natural language processing. For example, in medical notes, numerical data, such as heart rate, blood pressure, blood test results, are important bases for medical diagnosis and treatment. Interpretation of those medical notes requires a correct understanding of the numerical data contained therein, through semantic classification of numerical data in a natural language context. While many solutions exist to semantically classify words in natural language, they do not work effectively for classifying numbers based on their semantics within the natural language context. Traditional rule-based pattern matching algorithm is one of such solutions. It requires a priori knowledge of all possible rules/criteria in order to classify numbers, which is inefficient and poorly scalable.

Accordingly, there exists a continuing need for methods and systems for semantic classification of numerical data in a natural language context. The disclosed methods and systems can be used in healthcare, financial, legal, and accounting services.

SUMMARY OF THE INVENTION

This disclosure provides a method for processing numerical data within a natural language context. The method includes detecting in a natural language text segment the presence of numerical data including one or more numbers. Upon determining the presence of numerical data in the text segment, the method includes extracting the numbers and words surrounding the numbers and within a window of a predetermined length. The method also includes creating a word vector for each of the extracted words and determining the most correlated feature of the extract words by inputting the word vector for each of the extracted words into a first machine learning module. The method further includes associating the most correlated feature of the extracted words with the numbers and classifying the natural language text segment by inputting the numbers and the associated most correlated feature into a second machine learning module.

In some embodiments, the method may also include providing a medical diagnosis based on the numerical data and the classification of the natural language text segment. In some embodiments, the method may include generating a treatment plan based on the medical diagnosis.

In some embodiments, the first machine learning module includes a convolutional neural network. In some embodiments, the step of creating the word vector is performed by using a Word2Vec algorithm. In some embodiments, the step of determining the most correlated feature of the extract words is performed by using a max pooling algorithm. In some embodiments, the second machine learning module includes a feedforward neural network. In some embodiments, the feedforward neural network includes a softmax layer.

In some embodiments, the step of classifying the natural language text segment includes creating a feature vector for the most correlated feature of the extract words and inputting the feature vector into the second machine learning module.

In some embodiments, the natural language text segment includes a paragraph, a sentence, or a phrase. In some embodiments, the natural language text segment includes a portion of a medical note. In some embodiments, the window has the predetermined length of six words, such that three words are positioned before and after the numbers. In some embodiments, the first and second machine learning modules are trained by using a gradient descent algorithm.

This disclosure also provides a system for processing numerical data within a natural language context. The system includes a non-transitory, computer-readable memory; one or more processors; and a computer-readable medium containing programming instructions that, when executed by the one or more processors, cause the system to: detect in a natural language text segment the presence of numerical data including one or more numbers; upon determining the presence of numerical data in the text segment, extract the numbers and words surrounding the numbers, the words being within a window of a predetermined length; create a word vector for each of the extracted words; determine the most correlated feature of the extract words by inputting the word vector for each of the extracted words into a first machine learning module; associate the most correlated feature of the extracted words with the numbers; and classify the natural language text segment by inputting the numbers and the associated most correlated feature into a second machine learning module.

In some embodiments, the system may provide a medical diagnosis based on the numerical data and the classification of the natural language text segment. In some embodiments, the system may generate a treatment plan based on the medical diagnosis.

In some embodiments, the first machine learning module comprises a convolutional neural network. In some embodiments, the system may create the word vector by using a Word2Vec algorithm. In some embodiments, the system may determine the most correlated feature of the extract words by using a max pooling algorithm. In some embodiments, the second machine learning module includes a feedforward neural network. In some embodiments, the feedforward neural network includes a softmax layer.

In some embodiments, the system may classify the natural language text segment further includes programming instructions configured to create a feature vector for the most correlated feature of the extract words and input the feature vector into the second machine learning module. In some embodiments, the natural language text segment includes a paragraph, a sentence, or a phrase. In some embodiments, the natural language text segment includes a portion of a medical note. In some embodiments, the window has the predetermined length of six words, such that three words are positioned before and after the numbers. In some embodiments, the system may train the first and second machine learning modules by using a gradient descent algorithm.

These and other features and advantages of the present invention will become more apparent from the following description when considered in connection with the accompanying drawings.

BRIEF DESCRIPTION OF THE DRAWINGS

FIG. 3 illustrates an example of a text segment containing numerical data in which an example of a six-word window is shown.

DETAILED DESCRIPTION OF THE INVENTION

The present disclosure describes machine learning-based methods and systems for semantically classifying numerical data in natural language context. A convolutional neural network is applied on embedded words around numbers for feature detection and selection. A feedforward neural network with inputs of numbers and their associated word features is trained jointly with the convolutional neural network to learn the semantics of the numbers and classification according to the natural language context. The convolutional neural networks, as a semantic feature detector, are harvested at the end of the training. This machine learning process is unique and inventive in that expected output of the semantic feature detector does not need to be known in advance.

In telehealth systems, often the entire flow of a hospital visit is captured in digital media. For example, the Massachusetts General Hospital employs a telehealth system that uses video conferencing. If all of these videos demonstrating how patients are treated by doctors were to be stored, it would provide additional data contains information previously unrecorded in electronic medical record systems which are increasingly being used across hospitals in the US. Such new medical data constitute a rich source of information that holds incredible potential for big data analysis and the development of new healthcare technologies. One way to unlock the potential of the new medical data available through the increasingly utilized of telehealth systems is the application of natural language processing (NLP). Natural language processing is a new field in computer science and linguistics focusing on helping machines process and understand natural language. Current natural language processing programs have demonstrated success in identifying keywords in clinical narratives and can be used to accurately identify patients with prostate cancer and to retrieve pertinent pathologic information from their electronic medical records (EMR).

The inventive features of the disclosed methods and systems include a natural language processing program built with neural networks that allow the program to learn what the natural language means. Such a natural language processing program serves an effective tool enable us to structure and organize the previously unusable data in a natural language format.

Figure 1:
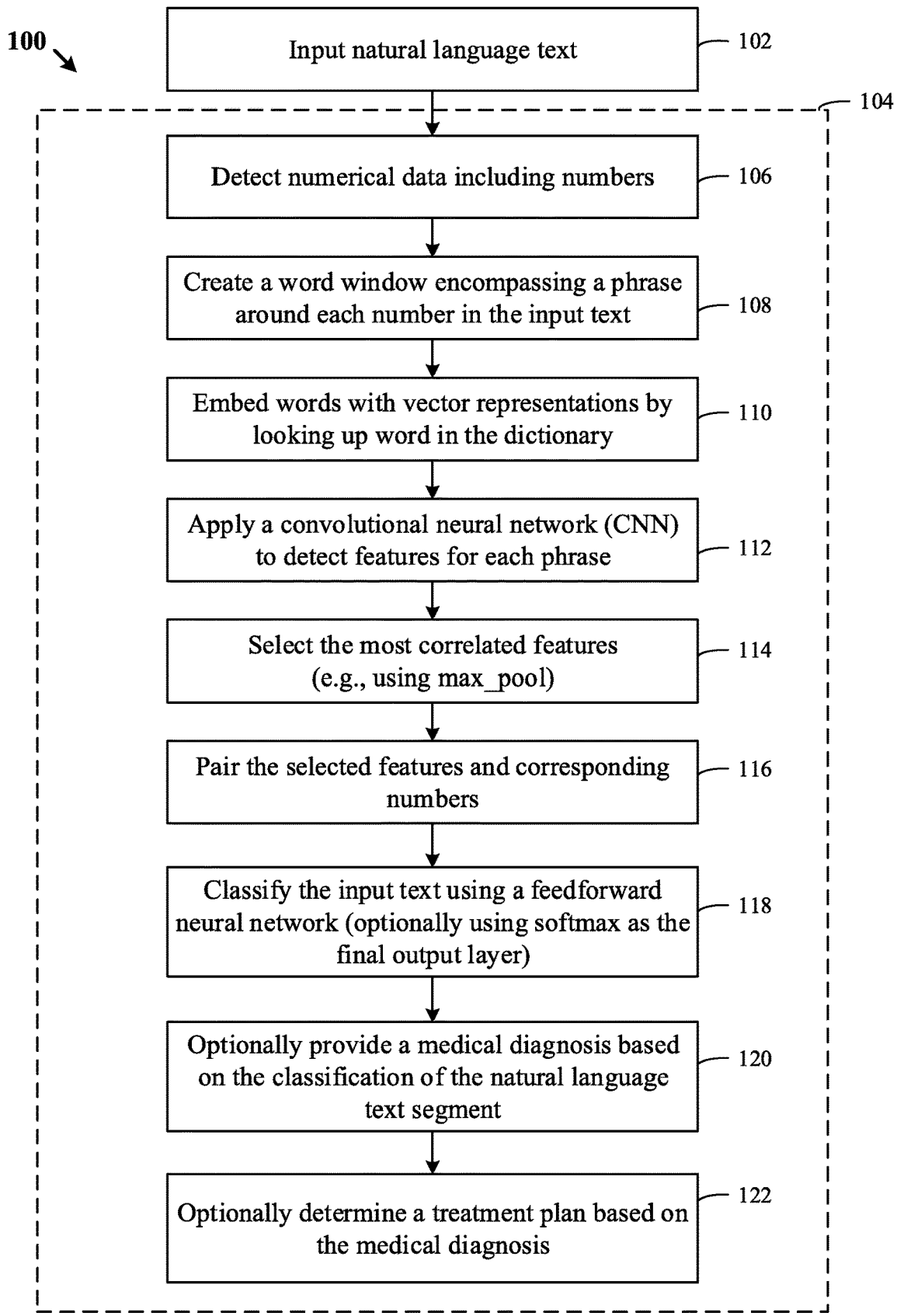
FIG. 1 illustrates a block/flow diagram showing a machine learning method and architecture for semantically classifying numerical data in a natural language context.

Referring now to FIG. 1, there is provided a block/flow diagram of a machine learning-based method 100 for processing numerical data in natural language context. The diagram illustrates the procedure and architecture of an example of the machine learning model. The method begins at 102 by providing a natural language text segment. The natural language text segment may include one or a plurality of paragraphs, sentences, or phrases or a combination thereof. The natural language text segment can be an official or unofficial language of any country or region. In some embodiments, the text segment may include texts presented in one or more languages. In addition, the natural language text segment may be provided in any fonts. The natural language text segment may or may not include numerical data. The numerical data may exist in a form of one or more numbers. The numbers can be continuous or discrete numbers. It would be understood by a person of ordinary skill in the art that the disclosed methods and systems can also be applied to other data types including, but not limited to, categorical and ordinal data types.

An example of a natural language text segment is shown in FIG. 3, which includes a portion of the text reproduced from a medical note. The text segment includes numerical data provided in different contexts and embedded in different features (e.g., temperature, blood pressure, heart rate, time). For example, the number 98.7 is surrounded by words including one or more keywords, such as "temperature" and "heart rate," which suggest the features temperature or heart rate is likely associated with the number. In another example, the number 128/61 is surrounded by words including "BP" which suggest the number is likely associated with blood pressure. At 106, the method continues with detecting numerical data in the provided natural language text segment. Upon determining the presence of the presence of numerical data including one or more numbers in the natural language text segment, at 108, the method may include creating a word window of a predetermined length (e.g., 10 words, 8 words, 6 words, 4 words). The word window, as shown in FIG. 3, is applied to each number detected and covers the number in the center of the window. For example, the window may have a length of 6 words, in which 3 consecutive words are positioned before the detected number and 3 consecutive words positioned after the detected number. The numbers and the words surrounding the numbers and within the window are then extracted and processed as inputs into one or more machine learning modules (e.g., convolutional neural network (CNN)). In some embodiments, padding may be required when the number is located in the front or at the end of a sentence, a phrase, or a paragraph. The "padding" features may be added to the beginning and the end of the sentence to cause the first several words and the last several words to be in the center of their window. Padding refers to the process of placing a "dummy" word before the sentence and after the sentence to ensure every word to be tagged in the sentence is generally in the middle of the window when a machine learning model is applied.

At 110, the method includes looking up the extracted words associated with the numbers in a dictionary. The dictionary contains an indexed lookup table to associate a word with a multidimensional word vector. The method further includes embedding each word with a vector representation. In embedding the extracted words with vector representations, the method may use a Word2Vec algorithm.

Word2Vec is a group of related models that are used to produce word embeddings. These models are shallow, two-layer neural networks that are trained to reconstruct linguistic contexts of words. Word2Vec takes as its input a large corpus of text and produces a vector space, typically of several hundred dimensions, with each unique word in the corpus being assigned a corresponding vector in the space. Word vectors are positioned in the vector space such that words that share common contexts in the corpus are located in close proximity to one another in the space.

At 112, the method includes applying a first machine learning module to detect one or more features for a phrase constituted by the extracted words. The features for the phrase, in a medical note context, may include, without limitation, blood pressure (BP), cholesterol (LDL and HDL), thyroid-stimulating hormone (TSH), body temperature, blood sugar level, bone mineral density, complete blood count, body mass index (BMI), C-Reactive Protein (CRP), waist size.

In some embodiments, the first machine learning module may include a convolutional neural network (CNN). In machine learning, a convolutional neural network (CNN or ConvNet) is a group of deep, feed-forward artificial neural networks. CNNs are most commonly applied to analyzing and classifying images, clustering images based on similarity (e.g., photo search), and performing object recognition within scenes. For example, CNNs can be used to identify faces, individuals, street signs, tumors, platypuses, and many other characteristics of imagery data. CNNs use a variation of multilayer perceptrons, designed to require minimal preprocessing. CNNs use relatively little pre-processing compared to other image classification algorithms. This means that the network learns the filters that were hand-engineered in traditional algorithms. This independence from prior knowledge and human effort in feature design is a major advantage of CNNs. Applications of CNNs include image and video recognition, recommender systems, and natural language processing. Typically, a CNN consists of an input and an output layer, as well as multiple hidden layers. The hidden layers of a CNN further consist of convolutional layers, pooling layers, fully connected layers and normalization layers. Convolutional layers apply a convolution operation to the input, passing the result to the next layer.

At 114, the method may include selecting the most correlated features for the phrase associated with the numbers. Selecting the most correlated features can be achieved by local or global pooling layers contained in convolutional networks, which combine the outputs of neuron clusters at one layer into a single neuron in the next layer. For example, the method may utilize a max pooling algorithm that uses the maximum value from each of a cluster of neurons at the prior layer. As shown in FIG. 3, for the number 98.7, the method may determine that the most correlated feature associated with the number is body temperature, instead of heart rate. Similarly, for the number 160/62, the method may determine that the most correlated feature is blood pressure, instead of body temperature.

At 116, after the most correlated feature for the phrase is selected, the method may further include pairing the selected feature with the corresponding number. In so doing, the method associates the selected feature and the number such that the associated number with the feature is in an expression format that is commonly recognized by a machine learning model. The above-described processes powered by a CNN accomplish at least the following goals: (1) detecting numbers in a natural language text segment; (2) determining the word context in which the numbers reside; (3) detecting features based on the word context; (4) determining the most correlated features associated with the numbers; and (5) reassembling the features with the numbers.

At 118, the method may further include classifying the natural language text segment by using a second machine learning module by providing above reassembled features and numbers as inputs. In some embodiments, the method may also include creating a feature vector to represent the selected features, such that the feature vector representing the selected features are provided as inputs into the second machine learning module. The second machine learning module may include a feedforward neural network. In some embodiments, the feedforward neural network may include softmax as the final output layer.

A feedforward neural network consists of a (possibly large) number of simple neuron-like processing units, organized in layers. Every unit in a layer is connected to all the units in the previous layer. Each connection may have a different strength or weight. The weights on these connections encode the knowledge of a network. Often the units in a neural network are also called nodes. Data enters at the inputs and passes through the network, layer by layer, until it arrives at the outputs. During normal operation, that is when it acts as a classifier, there is no feedback between layers. This is why they are called feedforward neural networks.

The feedforward neural network may employ softmax function as the final output to classify the paragraph according to their numerical features. Softmax function is a function turns real values into possibilities that sum to one. The softmax function is used in various multiclass classification methods, such as multinomial logistic regression (also known as softmax regression), multiclass linear discriminant analysis, naive Bayes classifiers, and artificial neural networks. Alternatively, the feedforward neural network may use a sigmoid function as the final output to classify the paragraph according to their numerical features. Softmax function and sigmoid function differ in that the sigmoid function is generally used for the two-class logistic regression, whereas the softmax function is mainly used for the multiclass logistic regression (a.k.a. MaxEnt, multinomial logistic regression, softmax Regression, Maximum Entropy Classifier).

The method may additionally include outputting a classification of the natural language text segment. For example, the method may likely classify a phrase in the natural language text segment containing "temperature was 104.2 degrees," as shown in FIG. 3, as "high." Likewise, the method may likely classify a phrase in the natural language text segment containing "Temp 98.6" as "normal."

Additionally and/or optionally, the method may include providing a medical diagnosis based on the classification of the natural language text segment. For example, based on the classification of a temperature number and feature, i.e., 104.2 degrees, the method may include determining that the patient may have a (high) fever. Further, the method may also include providing a medical diagnosis related to the cause of a fever, for example, bacterial infection or viral infection. As the disclosed machine learning model can be trained by providing medical data including diagnosis and prescribed treatment plans as inputs, it is capable of determining a treatment plan for a patient based on the diagnosis. For example, if a patient is determined to have a high fever caused by bacterial infection, the method may include providing a treatment plan having one or more antibiotics (e.g., Amoxicillin, Flucloxacillin, Penicillin G, Penicillin V, Pivmecillinam, Tazocin, Timentin) and/or pain relievers and fever reducers (e.g., Tylenol, Aspirin, Aleve, Advil, Motrin).

Figure 2:
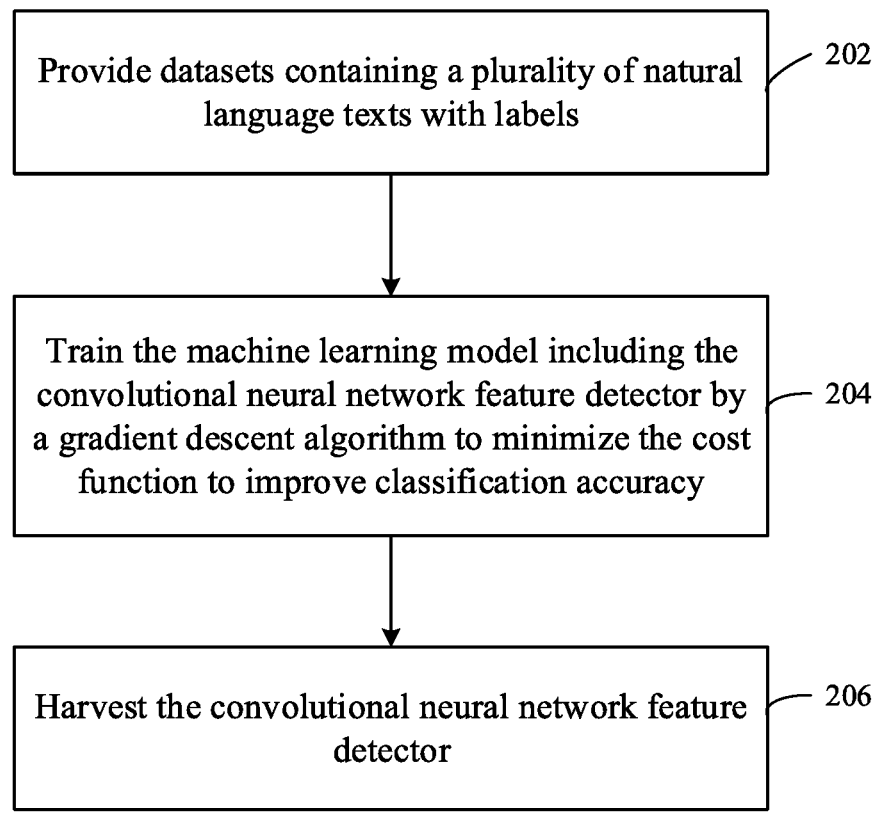
FIG. 2 illustrates an example of a process to train a machine learning model.

Steps 106, 108, 110, 112, 114, 116 and 118 constitute the machine learning model 104. With reference to FIG. 2, at 202, to train the machine learning model 104, the inputs including the numbers from the training set and the context vectors of the training set and the expected outputs including the labels of the training set are provided into the neural network. Generally, the more data with correct labels are provided to train the machine learning model, the more accurate the machine learning model will be.

At 204, the method may include using a gradient descent algorithm to minimize the cost function and improve the classification accuracy. Gradient descent is an optimization algorithm used to minimize some function by iteratively moving in the direction of steepest descent as defined by the negative of the gradient. In machine learning, gradient descent is used to update the parameters of the model. Parameters refer to coefficients in linear regression and weights in neural networks. A cost function shows the level of accuracy of a model at making predictions for a given set of parameters. The cost function has its own curve and its own gradients. The slope of this curve indicates how to update our parameters to make the model more accurate.

At 204, after training, the machine learning model is harvested, which can be used for numerical feature detection and/or numerical data classification.

The following non-limiting examples further illustrate certain aspects of the present invention.

EXAMPLES

Currently, numerical data can be extracted with some success using regular expressions to recognize patterns in the text. However, because most of the natural language is incredibly flexible in structure, refining a regular expression to correctly extract the meaning of the numbers is time-consuming and often impractical. For example, these three sentences are extracted from various clinical notes:

The patient's temperature was 95.3, blood pressure 102/82, heart rate 70 s, respiratory rate 16, 100% on SIMV.

On admission to the floor, temperature was 97.8, 113, ranging 95 to 113, respiratory rate 17, blood pressure ranging 120 to 150/90 s, 95% on room air.

His vital signs on presentation to the OSH were: Temp 103, BP 89/30, HR 116-138, RR 28, 97% on 2 L. His WBC was 15 (73 N, 11 L), CPK 253, (MB 21.5, Index 8.5), trop I 2.88. Glucose was 310.

These three sentences all refer to similar data, but in completely different expression formats characterized by different vocabulary and grammatical structures. To build a regular expression to correctly capture the meaning of all the numbers in these sentences would be an arduous process itself. It is an even more daunting task, considering that in practice the expression of similar numerical information in a natural language may use a wide variety of formats.

To demonstrate the utility and effectiveness of the disclosed systems and methods in processing numerical data within a natural language context, a model implementing the disclosed methods was built using neural networks geared towards understanding the numerical data within its natural language context. It is of note that the model was able to predict with 96% accuracy whether a section from clinical notes is referring to a patient with a fever, no fever, high blood pressure, or normal blood pressure.

The model includes a neural network for word embeddings. The word embedding are fed into a multi-layer convolutional neural network. The word embeddings are used as representations of the contexts of the numbers. Convolutional neural networks are commonly used for image recognition because they excel in identifying local features of data. In images, this translates to identifying edges. For data sets containing natural language texts, however, the convolutional neural network is used to identify the local characteristics of the contexts of the numbers. The neural network is based on the theory that the meaning of a word is essentially defined by the context of the word. This is the same theory behind the Word2Vec code which creates multi-dimensional vector embeddings for words based on the contexts surrounding the word.

The model employs the machine learning principle by allowing the machine to learn the meaning behind numbers. To represent the context of the numbers, word embedding for words within a window of a predetermined length and surrounding the numbers in the text. Both the context embeddings of the numbers and the numbers are provided as inputs into a convolutional neural network. Using the correct diagnoses of the sentences (e.g., high fever, high blood pressure) as the expected output, the model is trained to learn the meanings behind the numbers. After it is trained, the model accurately predicts whether a new selection of a natural language from clinical notes meant "high fever" or "high blood pressure."

To train and test the effectiveness of the model, the public Mimic III database was used. The database contains anonymized records from the Beth Israel Deaconess Medical Center of approximately 58,976 hospital admissions. To preprocess the data, all the sentences in the clinical notes that contained numbers were extracted. As the next step, all the numbers, as well as the words surrounding the numbers and within the word window, were used as the context. All of the context words were then embedded into multidimensional vectors to give them a mathematical representation. These vectors and the numbers were then used as the inputs into the convolutional neural network.

To better train the model, a large amount of correctly labeled data would be necessary. However, the clinical notes in the public Mimic III database do not have corresponding labels in structured tables for the temperature and blood pressures mentioned. To this end, in addition to the records of the public Mimic III database, artificial training data were generated by combining random words and a number, with a keyword in the sentence to signal the meaning of the number. For example, a random sentence with a random number was generated, and the keyword was inserted into the random sentence. 10,000 such sentences were generated for training the model. With this generated data, a labeled dataset (e.g., each sentence has a corresponding label for whether the sentence is concerning about "fever," "high blood pressure," or neither) was created. To train the model, the inputs, including the numbers from the training set and the context vectors of the training set, and the expected outputs, including the labels of the training set, were provided into the neural network.

To test the model, the data from the mimic database containing data preprocessed in the same way (context vectors and numbers), as described above. To determine the accuracy of the neural network's outputs, regular expressions to parse of the clinical notes were used. 1000 sentences that could be confidently labeled with "high fever" or "high blood pressure" were used to test the accuracy of our neural network. Out of the 1000 sentences used to test the model, the model identified 960 diagnoses correctly for a 96% accuracy rate. The incorrect diagnoses were often for numbers that were on the border of being "high" (e.g., 99.0-degree temperature being identified as a fever where it was labeled as normal temperature).

After examining the final values of the filters, a strong correlation was found between the final values of the filters and the type of number. For example, all of the "temperature" numbers were clustered strongly, and all of the "blood pressure" numbers were clustered far way with low standard deviations.

Figure 4:
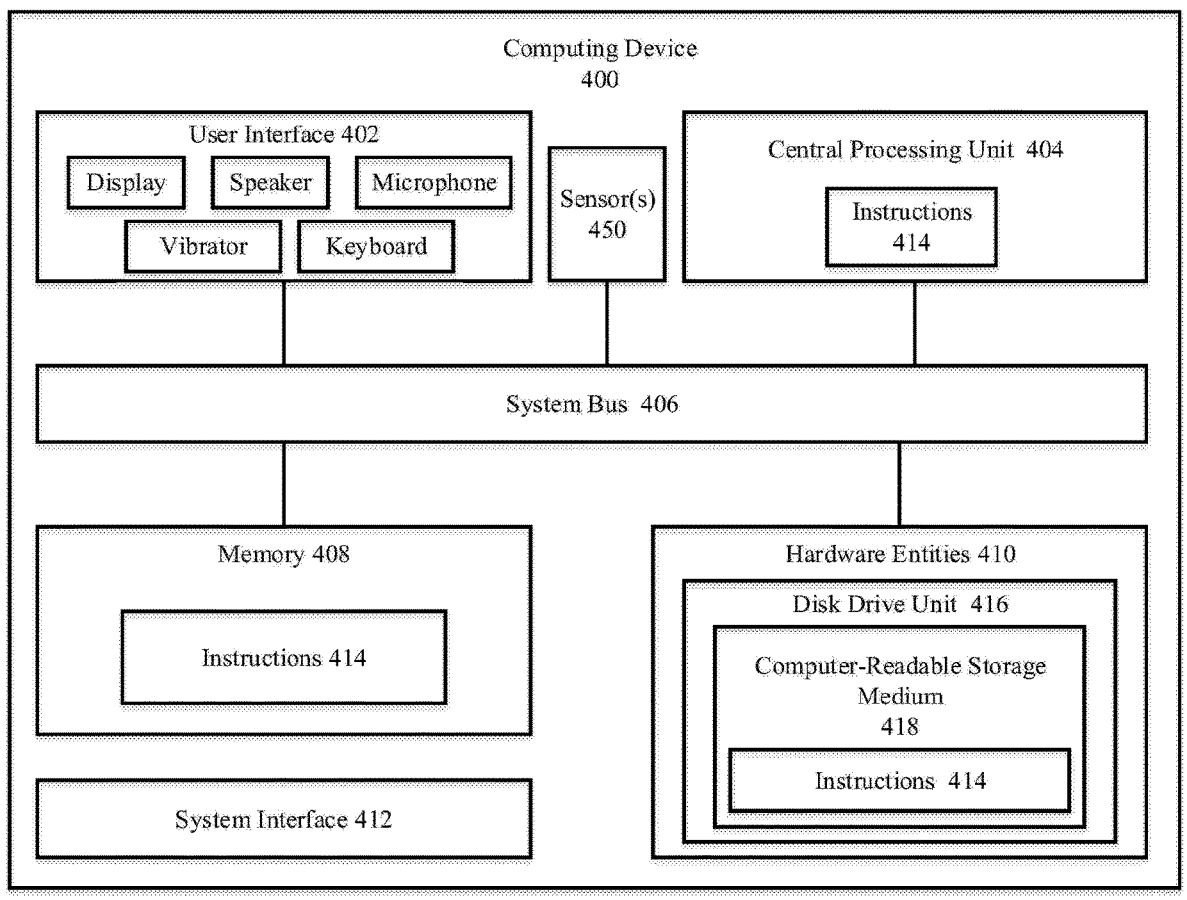
FIG. 4 illustrates an exemplary architecture of a computing device for implementing the disclosed methods.

The above-illustrated steps can be implemented in one or more computing systems. Referring now to FIG. 4, a computing system 400 is generally configured to perform operations for facilitating the connection of peripheral and central nerves output signatures of variability through the same statistical platform. As such, the computing system 400 includes a plurality of components 402-412. The computing system 400 can include more or fewer components than those shown in FIG. 4. However, the components shown are sufficient to disclose an illustrative embodiment implementing the present solution.

The hardware architecture of FIG. 4 represents one embodiment of a representative computing device configured to facilitate the connection of peripheral and central nerves output signatures of variability through the same statistical platform. As such, the computing system 400 implements methods of the present solution.

The computing system 400 may include a system interface 412, a user interface 402 (e.g., a keyboard for data input and a display for data output), a Central Processing Unit ("CPU") 404, a system bus 406, a memory 408 connected to and accessible by other portions of the computing system 400 through system bus 406, and hardware entities 410 connected to system bus 406. At least some of the hardware entities 410 perform actions involving access to and use of memory 408, which can be a Random Access Memory ("RAM"), a disk driver and/or a Compact Disc Read Only Memory ("CD-ROM"). System interface 412 allows the computing system 400 to communicate directly or indirectly with external devices (e.g., sensors, servers, and client computers).

The computing device 400 may also include sensors 450. The present solution is not limited in this regard. For example, in other scenarios, the sensors are separate devices from the computing device 400. A communications link (wired or wireless) is provided for enabling communications between the computing device 400 and sensors. In all cases, sensors 450 are coupled to a human or animal subject for obtaining data from at least one physiological relevant signal of the subject. The sensor can include, but is not limited to, an accelerometer, a gyroscope, a motion sensor, a vibration sensor, a position sensor, a restoration sensor, and/or a medical sensor (e.g., an electromyography sensor, an electrocardiogram sensor, an RIP sensor, an Mill sensor, etc.).

Hardware entities 410 may include microprocessors, Application Specific Integrated Circuits ("ASICs") and other hardware. Hardware entities 410 can include a microprocessor programmed to facilitate the connection of peripheral and central nerves output signatures of variability through the same statistical platform.

The hardware entities 410 may include a disk drive unit 416 including a computer-readable storage medium 418 on which is stored one or more sets of instructions 414 (e.g., software code) configured to implement one or more of the methodologies, procedures, or functions described herein. The instructions 414 can also reside, completely or at least partially, within the memory 408 and/or the CPU 404 during execution thereof by the computing system 400. The components 408 and 404 also can constitute machine-readable media. The term "machine-readable media," as used here, refers to a single medium or multiple media (e.g., a centralized or distributed database, and/or associated caches and servers) that store the one or more sets of instructions 414. The term "machine-readable media," as used here, also refers to any medium that is capable of storing, encoding or carrying a set of instructions 414 for execution by the computing system 400 and that cause the computing system 400 to perform any one or more of the methodologies of the present disclosure.

Notably, the present solution can be implemented in a single computing device as shown in FIG. 4. The present solution is not limited in this regard. Alternatively, the present solution can be implemented in a distributed network system. For example, the present solution can take advantage of multiple CPU cores over a distributed network of computing devices in a cloud or cloud-like environment. The distributed network architecture ensures that the computing time of the statistics and enhanced functionality is reduced to a minimum, allowing end-users to perform more queries and to receive reports at a faster rate. The distributed network architecture also ensures that the implementing software is ready for being deployed on an organization's internal servers or cloud services in order to take advantage of its scaling abilities (e.g., request more or fewer CPU cores dynamically as a function of the quantity of data to process or the number of parameters to evaluate).

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto-optical disks; and CD ROM and DVD-ROM disks. To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application and receiving responsive messages from the user in return.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other units suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, subprograms, or portions of code. A computer program can be deployed to be executed on one computer or on multiple computers that are located at one site or distributed across multiple sites and interconnected by a data communication network.

This specification uses the term "configured" in connection with systems and computer program components. For a system of one or more computers to be configured to perform particular operations or actions means that the system has installed on its software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially be claimed as such, one or more features from a claimed combination can in some cases be excised from the combination, and the claimed combination may be directed to a sub combination or variation of a sub combination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" (or "comprises") means "including (or includes), but not limited to." When used in this document, the term "exemplary" is intended to mean "by way of example" and is not intended to indicate that a particular exemplary item is preferred or required.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method for processing numerical data within a natural language context, the method comprising:
    detecting in a natural language text segment the presence of numerical data comprising one or more numbers;
    extracting the numbers detected and words surrounding the numbers, the words being within a window of a predetermined length of six words such that three words are positioned before and after the numbers;
    creating a word vector for each of the extracted words;
    determining the most correlated feature of the extracted words by inputting the word vector for each of the extracted words into a first machine learning module, wherein the first machine learning module comprises a convolutional neural network;
    associating the most correlated feature of the extracted words with the numbers; and
    classifying the natural language text segment by inputting the numbers and the associated most correlated feature into a second machine learning module, wherein the second machine learning model comprises a feedforward neural network, and classifying the natural language text segment comprises creating a feature vector for the most correlated feature of the extract words and inputting the feature vector into the second machine learning module.

2. The method of claim 1, further comprising:
    providing a medical diagnosis based on the numerical data and the classification of the natural language text segment.

3. The method of claim 2, further comprising:
    generating a treatment plan based on the medical diagnosis.

4. The method of claim 1, wherein the step of creating the word vector is performed by using a Word2Vec algorithm.

5. The method of claim 1, wherein the step of determining the most correlated feature of the extract words is performed by using a max pooling algorithm.

6. The method of claim 1, wherein the feedforward neural network comprises a softmax layer.

7. The method of claim 1, wherein the natural language text segment comprises any of a paragraph, a sentence, a phrase, a portion of a medical note, and a combination thereof.

8. The method of claim 1, wherein the first and second machine learning modules are trained by using a gradient descent algorithm.

9. A system for processing numerical data within a natural language context, comprising:
    a non-transitory, computer readable memory;
    one or more processors; and
    a computer-readable medium containing programming instructions that, when executed by the one or more processors, cause the system to:
    detect in a natural language text segment the presence of numerical data comprising one or more numbers;
    extract the numbers detected and words surrounding the numbers, the words being within a window of a predetermined length of six words such that three words are positioned before and after the numbers;
    create a word vector for each of the extracted words;
    determine the most correlated feature of the extracted words by inputting the word vector for each of the extracted words into a first machine learning module, wherein the first machine learning module comprises a convolutional neural network;
    associate the most correlated feature of the extracted words with the numbers; and
    classify the natural language text segment by inputting the numbers and the associated most correlated feature into a second machine learning module, wherein the second machine learning module comprises a feedforward neural network, and wherein the programming instructions configured to classify the natural language text segment further comprise programming instructions configured to create a feature vector for the most correlated feature of the extract words and input the feature vector into the second machine learning module.

10. The system of claim 9, further comprising programming instructions configured to:
    provide a medical diagnosis based on the numerical data and the classification of the natural language text segment, determine a treatment plan based on the medical diagnosis, create the word vector by using a Word2Vec algorithm, and/or determine the most correlated feature of the extract words by using a max pooling algorithm.

11. The system of claim 9, wherein the feedforward neural network optionally comprises a softmax layer.

12. The system of claim 9, wherein the natural language text segment comprises any of a paragraph, a sentence, a phrase, a portion of a medical note, and a combination thereof.

13. The system of claim 9, further comprising programming instructions configured to train the first and second machine learning modules by using a gradient descent algorithm.

* * * * *